(12) United States Patent
Nemoto

(10) Patent No.: US 7,422,514 B2
(45) Date of Patent: Sep. 9, 2008

(54) DENTAL CROWN POLISHING APPARATUS

(76) Inventor: Timothy Tamio Nemoto, 3/5575 Oak Street, Vancouver, British Columbia (CA) V6M 2V5

( * ) Notice: Subject to any disclaimer, the term of this patent is extended or adjusted under 35 U.S.C. 154(b) by 224 days.

(21) Appl. No.: 11/581,792

(22) Filed: Oct. 16, 2006

(65) Prior Publication Data
US 2007/0093188 A1 Apr. 26, 2007

(30) Foreign Application Priority Data
Oct. 21, 2005 (JP) .............................. 2005-306564

(51) Int. Cl.
*B24B 5/00* (2006.01)
*B24B 29/00* (2006.01)
*B24B 47/02* (2006.01)
(52) U.S. Cl. ...................... 451/258; 451/287; 451/338
(58) Field of Classification Search ................. 451/285, 451/287, 580, 291, 338, 359, 363, 394, 464, 451/56
See application file for complete search history.

(56) References Cited

U.S. PATENT DOCUMENTS

| | | | | |
|---|---|---|---|---|
| 5,616,063 | A | * | 4/1997 | Okumura et al. ................ 451/1 |
| 5,643,067 | A | * | 7/1997 | Katsuoka et al. ............. 451/444 |
| 5,653,623 | A | * | 8/1997 | Kimura et al. ................. 451/72 |
| 5,782,675 | A | * | 7/1998 | Southwick .................... 451/56 |
| 5,839,947 | A | * | 11/1998 | Kimura et al. ............... 451/288 |
| 5,895,311 | A | * | 4/1999 | Shiotani et al. ................. 451/5 |
| 6,165,056 | A | * | 12/2000 | Hayashi et al. .............. 451/281 |
| 6,203,413 | B1 | * | 3/2001 | Skrovan ....................... 451/72 |
| 6,306,008 | B1 | * | 10/2001 | Moore ........................... 451/5 |
| 6,379,230 | B1 | * | 4/2002 | Hayashi et al. .............. 451/292 |
| 6,796,877 | B1 | * | 9/2004 | Bingham et al. ................ 451/5 |
| 6,916,231 | B2 | * | 7/2005 | Wakabayashi ................ 451/66 |
| 7,097,544 | B1 | * | 8/2006 | Tolles et al. .................... 451/66 |

FOREIGN PATENT DOCUMENTS

JP        2003-048145        2/2006

* cited by examiner

*Primary Examiner*—Alvin J. Grant
(74) *Attorney, Agent, or Firm*—Harness, Dickey & Pierce, P.L.C.

(57) ABSTRACT

A dental crown polishing apparatus has a motor, a ball bearing assembly around a shaft of the motor and having balls rotating and circularly moving around the motor shaft by receiving torque from the motor shaft, a brush assembly on the periphery of the ball bearing assembly, equipped with brushes contacting the ball to rotate and having bristles in the same direction as an axial direction of rotation and a tray opposite and open to the brush assembly to dispose a crown toward the brushes. The motor shaft is offset from the center of the brush assembly. The brush assembly moves in an orbital fashion by the rotation of the motor. The tray rotates separately from the brush assembly. The rotation of the tray is not synchronous with the rotation of the brush assembly. Dental crown polishing is achieved by the orbital movement of the brushes.

10 Claims, 11 Drawing Sheets

DENTAL CROWN POLISHING APPARATUS

CLAIM OF PRIORITY

This application claims the benefit of Japanese Patent Application No. 2005-306564 filed on Oct. 21, 2005, the entire contents of which are hereby incorporated by reference herein.

BACKGROUND OF THE INVENTION

1. Field of the Invention

The present invention relates to a dental crown polishing apparatus for polishing dental crowns and the like.

2. Description of the Related Art

Dental crowns, bridges, dentures and the like (hereinafter referred to collectively as "crowns") are produced in a dental crown laboratory. Typically, crowns are polished in the finishing stage. The crowns are machined to a complicated, uneven shape so as to give them the same capabilities as a natural tooth.

In the conventional polishing step, as shown in FIG. 11, a dental lathe or a hand piece 100 (hereinafter "hand piece or the like") is used and each crown 110 is polished individually by hand. In general, the hand piece or the like 100 is mounted with a disc-like polishing brush 102 disposed on a rotary shaft 101. The disc-like polishing brush 102 is so large compared to the size of the deeply uneven surface of the crown 110 that the deep grooves can not be polished precisely without breaking the crown 110.

The inventor of the present invention previously invented an orbital dental crown polishing device equipped with small brushes adequate to the task of polishing crowns one at a time, as disclosed in Japanese Laid-Open Patent Application Publication No. 2003-048145 ("Pat. Pub. No. 2003-048145"). FIG. 12 shows a side view of the device disclosed in Pat. Pub. No. 2003-048145. As shown in FIG. 12, a brush 151 is contact with the uneven surface of a crown 160 and the crown 160 is moved manually while a device 150 supplies fluid containing a polishing agent (polishing slurry) to the brush 151 so as to polish the surface of the crown 160. The apparatus 150 makes precise polishing of the crown 160 possible without damaging it.

However, the apparatus disclosed in Pat. Pub. No. 2003-048145 has room for further improvement. In particular, since it is necessary to hold each crown in hand and polish it, a great deal of time is required to polish many crowns, and consequently the cost of processing the crowns increases.

SUMMARY OF THE INVENTION

Accordingly, the present invention is conceived in light of the above-described circumstances, and has the purpose of providing a dental crown polishing apparatus capable of improving the efficiency of polishing the crowns and contributing to reducing the cost of the polishing process.

To achieve the above-described purpose, the present invention provides a dental crown polishing apparatus comprising:

a motor;

a ball bearing assembly arranged around a motor shaft of the motor and equipped with a plurality of balls which rotate on its axis and circularly move around the motor shaft by receiving torque from the motor shaft;

a brush assembly mounted on the outer periphery of the ball bearing assembly, equipped with brushes that contact the plurality of balls to rotate and that have bristles in the same direction as an axial direction of such rotation; and a tray disposed opposite and open to the brush assembly so as to direct a crown toward the brushes, wherein the brush assembly is attached to the motor shaft in a position offset from the center of the motor shaft, the brush assembly is able to move in orbital fashion by the rotation of the motor, the tray is able to rotate separately from the brush assembly, the rotation of the tray is not synchronous with the rotation of the brush assembly, and, the brushes polish the dental crown in an orbital movement.

Therefore, by setting multiple crowns in the tray and supplying polishing agent thereto, multiple crowns can be polished in a single polishing operation. Furthermore, since the brush rotates independently of the tray and moves orbitally, the crowns are polished while contacting the brush at multiple locations. As a result, even the most uneven parts of the crowns can be thoroughly polished.

In addition, according to one aspect of the present invention, the brush assembly comprises a power transmission means for transmitting torque to the tray, and the tray comprises a passive means for receiving torque from the power transmission means with a rotation permitting means for permitting the tray to rotate. The tray intermittently receives force in the direction of rotation by receiving the eccentric drive from the brush assembly through the passive means and rotates separately from the brush assembly.

Accordingly, even without providing a separate drive source for rotating the tray, by using only the motor for driving the brush assembly the brush assembly and the tray can be rotated separately from each other and the brush assembly is made to move orbitally.

In addition, according to another aspect of the present invention, the power transmission means comprises a first projecting member projecting from the periphery of the brush assembly and the passive means comprises a second projecting member projecting from the periphery of the tray.

Accordingly, caused by the orbital movement of the brush assembly; the drive force of the brush assembly is easily transmitted to the tray in the circumferential direction of the tray with a simple structure.

In addition, according to another and further aspect of the present invention, the rotation permitting means is a ball bearing assembly disposed between the tray and a pedestal positioned beneath the tray.

Accordingly, the tray receiving the drive force from the brush assembly rotates smoothly in the circumferential direction.

In addition, according to yet another and further aspect of the present invention, the dental crown polishing apparatus further comprises a means for adjusting the rotation of the tray.

Accordingly, when the tray receives the drive force from the brush assembly and rotates, resistance against the rotation can be adjusted, and thus a rotation of the tray that is suited to each polishing process can be achieved.

In addition, according to still another and further aspect of the present invention, the dental crown polishing apparatus further comprises a means for adjusting the distance of the tray from the brush assembly.

Therefore, without setting the crowns in the tray at the optimum height, good polishing can still be achieved. Moreover, by adjusting the height of the tray according to the extent of polishing, it is possible to accommodate a variety of polishing conditions.

In addition, according to still another and further aspect of the present invention, the dental crown polishing apparatus further comprises a means for adjusting the horizontal angle of the brush with respect to an open surface of the tray.

Accordingly, by setting the brush at a slight angle, it is possible to thoroughly polish even the deepest grooves, even if there is wide variation in the depth of the grooves in the uneven parts of the crowns.

The present invention improves the efficiency of polishing the crowns and contributes to reducing the cost of the polishing process.

Other features, objects and advantages of the present invention will be apparent from the following description when taken in conjunction with the accompanying drawings, in which like reference characters designate the same or similar parts throughout the figures thereof.

BRIEF DESCRIPTION OF THE DRAWINGS

FIG. 11 is a diagram illustrating the conventional method of polishing a crown or the like.

DETAILED DESCRIPTION OF THE PREFERRED EMBODIMENTS

Preferred embodiments of the present invention will now be described, with reference to the accompanying drawings.

Figure 1:
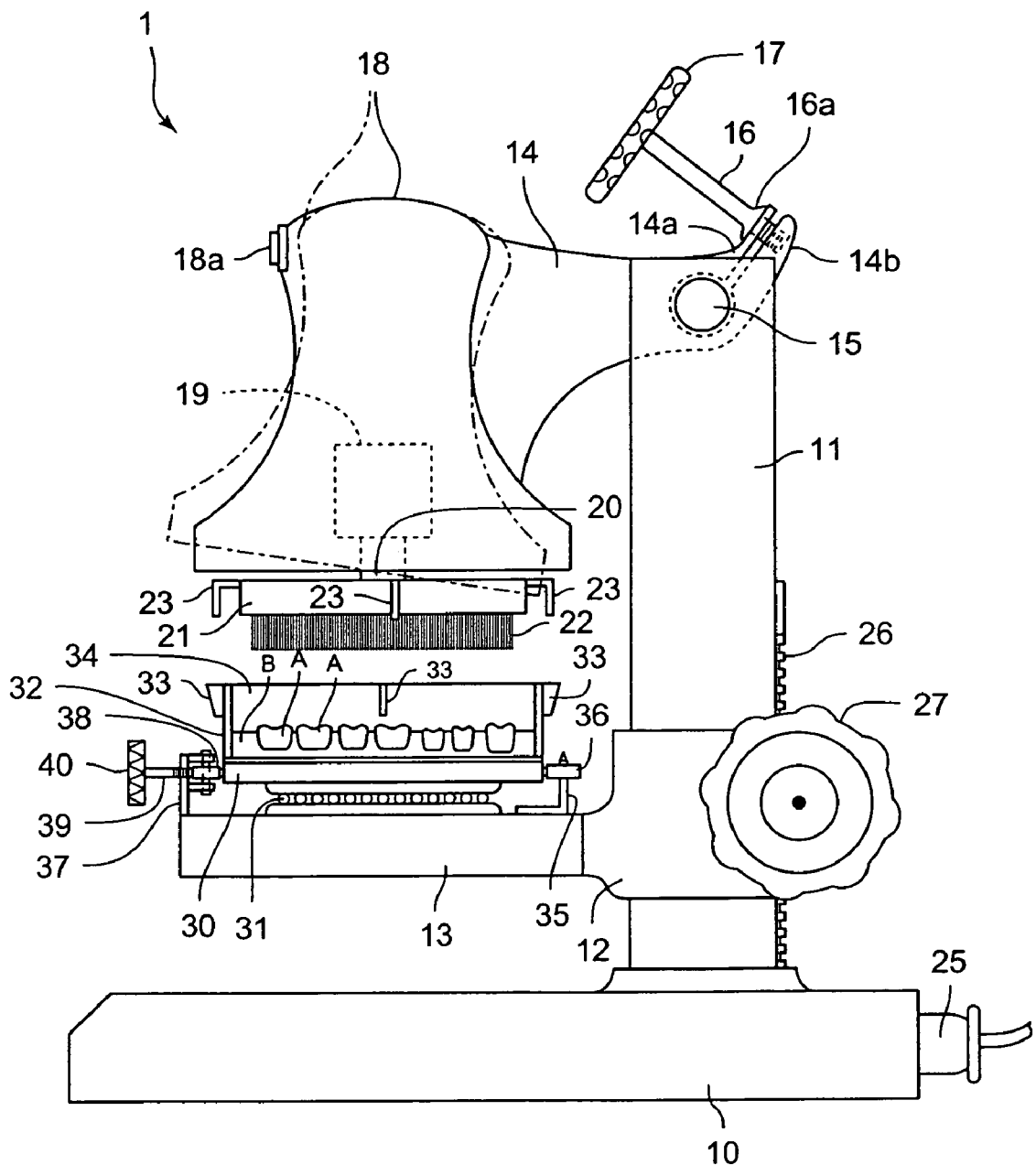
FIG. 1 shows a side view of the dental crown polishing apparatus according to an embodiment of the present invention.
Figure 2:
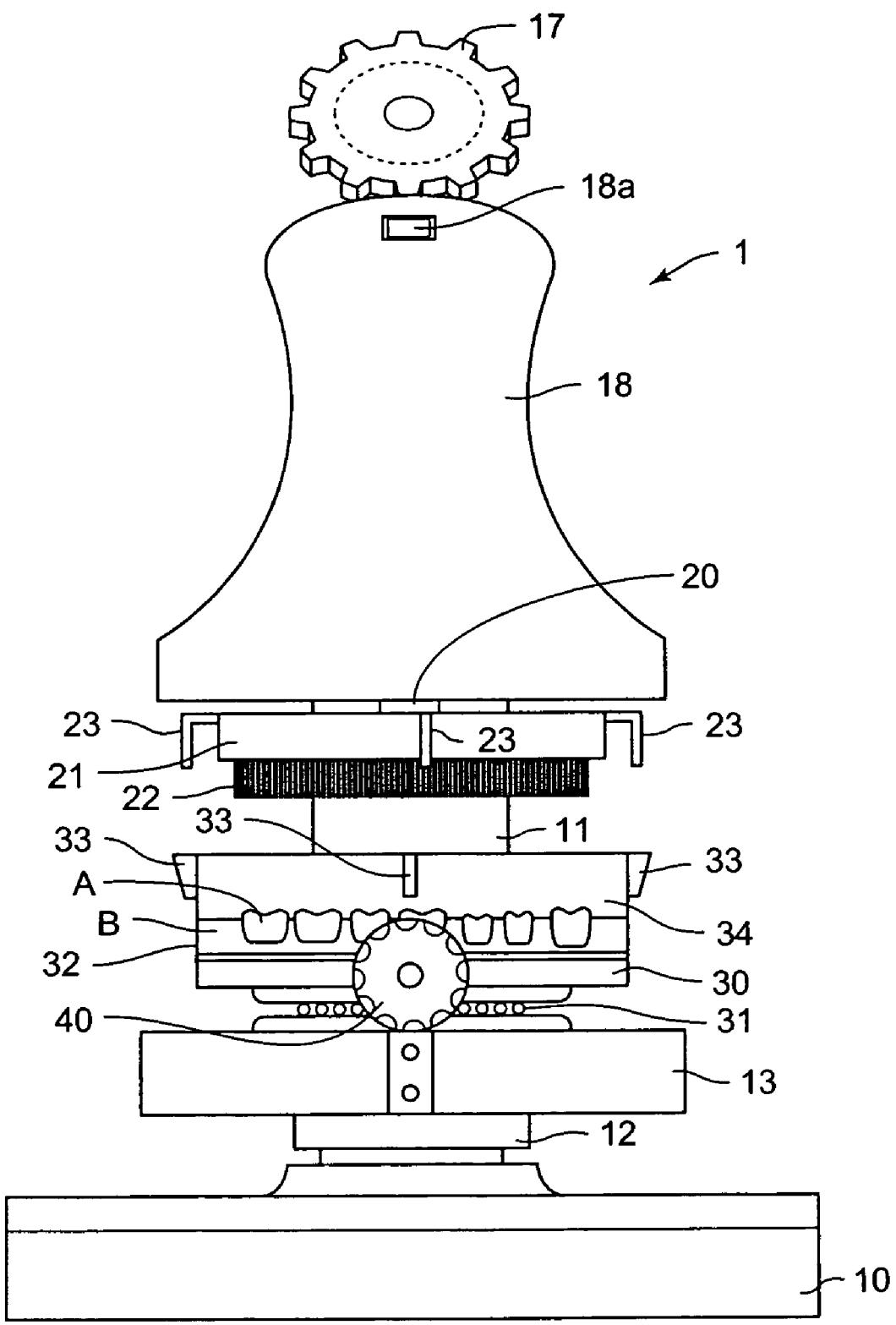
FIG. 2 shows a front view of the dental crown polishing apparatus according to an embodiment of the present invention.

FIG. 1 shows a side view of a dental crown polishing apparatus according to an embodiment of the present invention. FIG. 2 shows a front view of the dental crown polishing apparatus according to an embodiment of the present invention. It should be noted that, in the following description, up, down, left and right in FIG. 1 are called "top", "bottom", "front" and "rear", respectively.

The dental crown polishing apparatus 1 according to the present embodiment comprises a rectangular planar fixed base 10, a support post 11 disposed so as to protrude in a direction perpendicular to the fixed base 10 from a position offset from a center top point on the fixed base 10, an annular ring member 12 into which the support post 11 is inserted and which is mounted so as to be movable vertically in the direction of the length of the support post 11, a planar pedestal 13 connected to the ring member 12 and having a substantially square broad surface extended parallel to the top surface of the fixed base 10 toward a perpendicular line that penetrates the top of the fixed base 10, an arm 14 provided on top of the support post 11 and extended toward a perpendicular line that penetrates the top of the fixed base 10, and a head 18 connected to the arm 14 and disposed above the pedestal 13.

A cut of predetermined length is made in the top of the support post 11 from the top toward the bottom. One end of the arm 14 is inserted into this cut. The end of the arm 14 inserted into the cut is penetrated by a fixed shaft 15 inserted from a side of the support post 11 at substantially a right angle to the point at which the end of the arm 14 is inserted into the cut in the support post 11. One end of the arm 14 has two planar projecting parts 14a, 14b extended from the hole that is penetrated by the fixed shaft 15 to the tip of the end. The tips of the projecting parts 14a, 14b project beyond the cut in the support post 11. A shaft 16 penetrates the tip of the projecting part 14a. The shaft 16 has a handle at one end and a slot for a screw at the other end. The handle 17, the shaft 16, the fixed shaft 15 and the arm 14 form one example of a brush angle adjustment means. A flange part 16a having a diameter larger than the diameter of the screw hole is provided on the upstream end of the screw slot of the shaft 16 so as to allow the projecting part 14a to be pressed by being screwed toward the projecting part 14b of the shaft 16. A screw hole is formed on the surface opposite the projecting part 14a that is the tip of the projecting part 14b into which the tip of the side having the screw slot of the shaft 16 is screwed.

Accordingly, as the handle 17 is turned and the shaft 16 is screwed into the projecting part 14b, the gap between the projecting part 14a and the projecting part 14b narrows and the circumference of the fixed shaft 15 is tightened. Conversely, as the handle 17 is rotated so as to withdraw the shaft 16 from the projecting part 14b, the gap between the projecting part 14a and the projecting part 14b widens and the circumference of the fixed shaft 15 is loosened. As a result, after the handle 17 is turned so as to loosen the hold of the one end of the arm 14 on the fixed shaft 15 and the arm 14 is set to a desired angle, the handle 17 is then turned so as to tighten the hold of the one end of the arm 14 on the fixed shaft 15, enabling the head 18 to be held at a set angle. As shown in FIG. 1 by the solid lines and the dot-and-dash lines, the angle of the head 18 about the fixed shaft 15 can be changed.

The head 18 is substantially bell-shaped, the bottom of which is substantially flat. A switch 18a is provided on the outside of the head 18. A motor 19 (indicated by the dotted line in FIG. 1) is contained in the interior of the head 18. A power cord 25 is connected to one side of the fixed base 10. The power cord 25 is electrically connected to the motor 19. By plugging the power cord into a household outlet or the like and turning the switch 18a ON and OFF, the rotation of the motor 19 can be started and stopped. Although the motor 19 described in the present embodiment can run at several thousand to several tens of thousands of revolutions per minute, it is possible to use motors that can rotate at more or fewer revolutions per minute. Moreover, a variety of motors may be used for the motor 19, including a DC motor, an AC motor and a stepping motor.

A brush assembly 21 mounted on a projecting rotary shaft 20 that is coupled to the motor shaft of the motor 19 is provided on the bottom of the head 18 facing the pedestal 13. The brush assembly 21 is disc-shaped, and has brushes 22 on the surface facing the pedestal 13. A total of four first projecting members 23 spaced 90 degrees apart are connected to the periphery of the brush assembly 21. The first projecting members 23 have a L shape, extending beyond the edge of the brush assembly 21 in the direction of the diameter of the brush assembly 21 and then downward toward the pedestal 13 (below) at (substantially) a right angle. The first projecting members 23 are examples of a power transmission means (to be described later) that transmits the power of rotation to a tray on the pedestal 13.

The ring member 12 coupled to the pedestal 13 is mounted on the support post 11 in such a way as to engage a multi-stage stopper 26 provided on the rear of the support post 11 up to a optimum height from the bottom of the support post 11. A knob 27 for adjusting the tightness of the ring member 12 against the support post 11 is mounted on the ring member 12. At least one of the knob 27 and the multi-stage stopper 26 constitutes a means for adjusting the height of the tray. When moving the ring member 12 along the length of the support post 11, the knob 27 is turned to loosen the force with which the ring member 12 is held against the support post 11. When fixing the ring member 12 in place at an intermediate position along the support post 11, the knob 27 is turned to tighten the force with which the ring member 12 is held against the support post 11. The stopper 26 is a multi-stage one, and thus the ring member 12 can be moved up and down in stages.

A tray mounting plate 30 is disposed on the surface of the pedestal 13 facing the head 18. The tray mounting plate 30 is connected to the pedestal 13 through a ball bearing assembly 31. The ball bearing assembly 31 constitutes a means to permit the tray mounting plate 30 to rotate. A container (what is herein called a "tray") 32 is fixedly mounted on the tray mounting plate 30 with the open face towards the brushes 22. The side of the tray 32 is composed of a transparent cylindrical panel 34. It should be noted that the cylindrical panel 34 may be opaque or semi-transparent. A total of four second projecting members 33 spaced 90 degrees apart are connected to the periphery of the cylindrical panel 34. The second projecting members 33 are flat panels extending in the direction of the diameter of the tray 32. As will be described later, the second projecting members 33 constitute passive means for receiving torque from the first projecting members 23 of the brush assembly 21.

In the tray 32, for example, multiple dental crowns A fixed in a resin agent B can be placed (In FIG. 1 and in the remaining diagrams, although only some of the crowns A are given the reference designation "A", it is to be understood that reference designation A applies to all crowns depicted therein.). In FIG. 1 and FIG. 2, the cylindrical panel 34 is transparent, and thus the crowns are drawn as if they are visible from the outside. The exact method of polishing the crowns is described in detail later.

On the pedestal 13, a L-shaped roller mounting shaft 35 is fixedly mounted on the rear side of the tray mounting plate 30. A roller 36 is mounted on the roller mounting shaft 35 so as to contact the periphery of the tray mounting plate 30. The roller 36 thus contacts the side of the tray mounting plate 30 so as to enable the tray mounting plate 30 to rotate smoothly, without rolling. It should be noted that a plurality of rollers 36 may be provided around the periphery of the tray mounting plate 30. Moreover, a roller mounting plate 37 is fixedly mounted on the front of the tray mounting plate 30 at a position 180 degrees from the roller 36.

Figure 3:
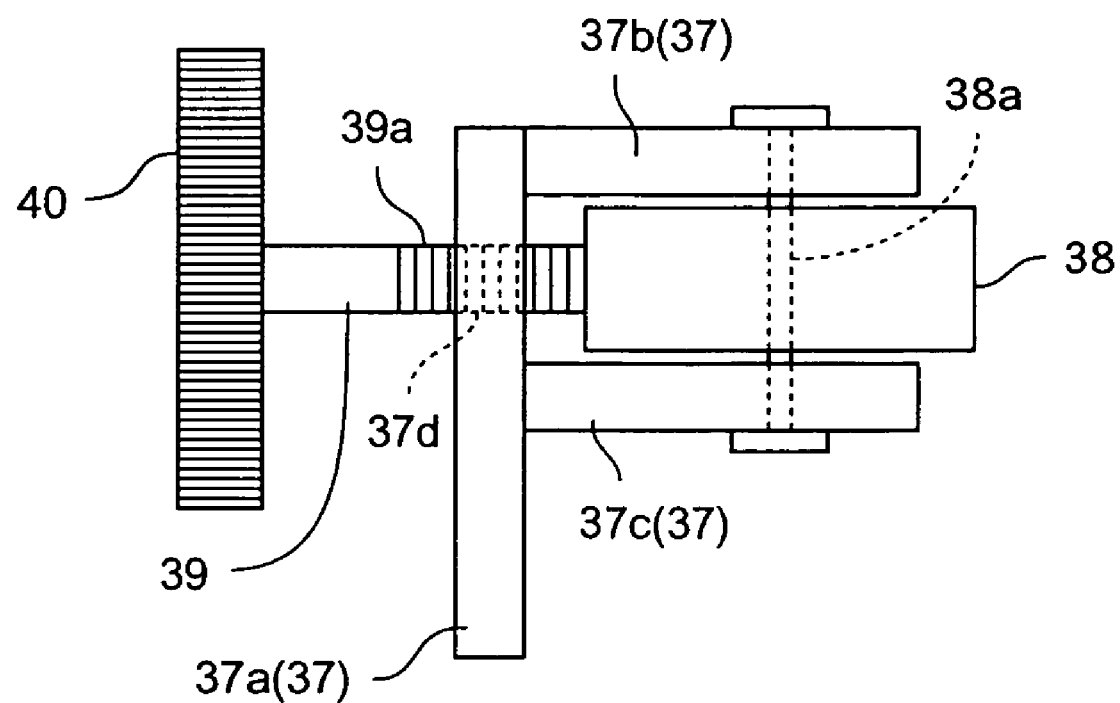
FIG. 3 shows an enlarged view of the area of the roller mounting plate shown in FIG. 1.

FIG. 3 shows an enlarged view of the area of the roller mounting plate 37.

The roller mounting plate 37 comprises a fixed vertical panel 37a that extends vertically from the pedestal 13 and two horizontal panels 37b and 37c extending substantially parallel to the top of the pedestal 13 in the direction of the tray mounting plate 30 from the fixed vertical panel 37a. The two horizontal panels 37b and 37c are fixedly mounted on the vertical panel 37a at positions separated in the vertical direction by a predetermined interval. A roller 38 whose center is penetrated by a rotary shaft 38a mounted vertically with respect to the horizontal panels 37b and 37c is provided between the horizontal panel 37b and the horizontal panel 37c. The roller 38 is provided between the horizontal panel 37b and horizontal panel 37c in such a state as to be rotatable while contacting the periphery of the tray mounting plate 30.

A shaft 39 is disposed on a side 180 degrees opposite the point of contact between the roller 38 and the tray mounting plate 30. The tip of the shaft 39 contacts the roller 38. A knob 40 is mounted on the other end of the shaft 39 on a side 180 degrees opposite the portion of the shaft 39 that contacts the roller 38. Screw threads 39a are cut into the shaft 39 over a predetermined length from the end of the shaft 39, and the threaded shaft 39a is screwed into a threaded through-hole 37d similarly provided on the vertical panel 37a of the roller mounting plate 37. Accordingly, as the knob 40 is turned and the shaft 39 is screwed toward the back of the apparatus, the tip of the shaft 39 strongly contacts the roller 38, which not only restrains the rotation of the roller 38 but also increases the resistance to the rotation of the tray mounting plate 30. In the present embodiment, the knob 40 and the shaft 39 constitute an example of rotation adjustment means.

Figure 4:
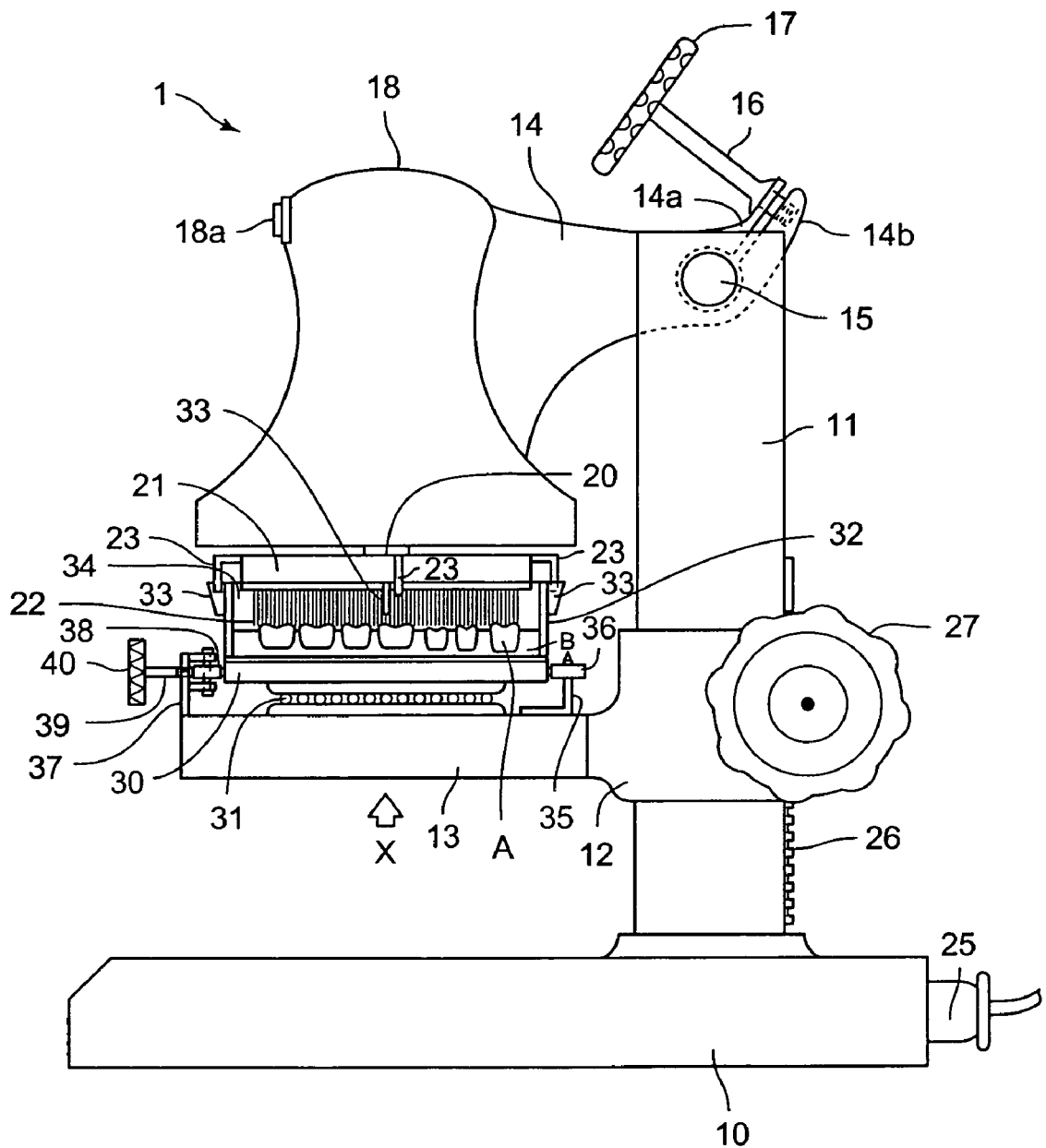
FIG. 4 shows a state in which the height of a pedestal is adjusted by lifting in the direction indicated by an arrow X to a position at which the brush contacts a crown in the tray in the dental crown polishing apparatus shown in FIG. 1.

FIG. 4 shows a state in which the height of the pedestal 13 is adjusted and the pedestal 13 is lifted in a direction indicated by an arrow X to a position at which the brushes 22 contact the crowns A in the tray 23 in the dental crown polishing apparatus shown in FIG. 1.

The brush assembly 21 has a disc-like shape of smaller diameter than the opening in the tray 32. In addition, a portion extending in the vertical direction of the first projecting members 23 contacts the second projecting members 33 provided around the periphery of the tray 32. The first projecting members 23 and the second projecting members 33 are each disposed 90 degrees apart around the periphery of the brush assembly 21 and the tray 32, respectively. Therefore, as shown in FIG. 3, when a given first projecting member 23 contacts one side of a given second projecting member 33, the remaining first projecting members 23 also contact the same sides of the remaining second projecting members 33. It should be noted that the number of the first projecting members 23 or the second projecting members 33 is not limited to the four described in the present embodiment, and may thus consist of one, two, three, or five or more.

Figure 5:
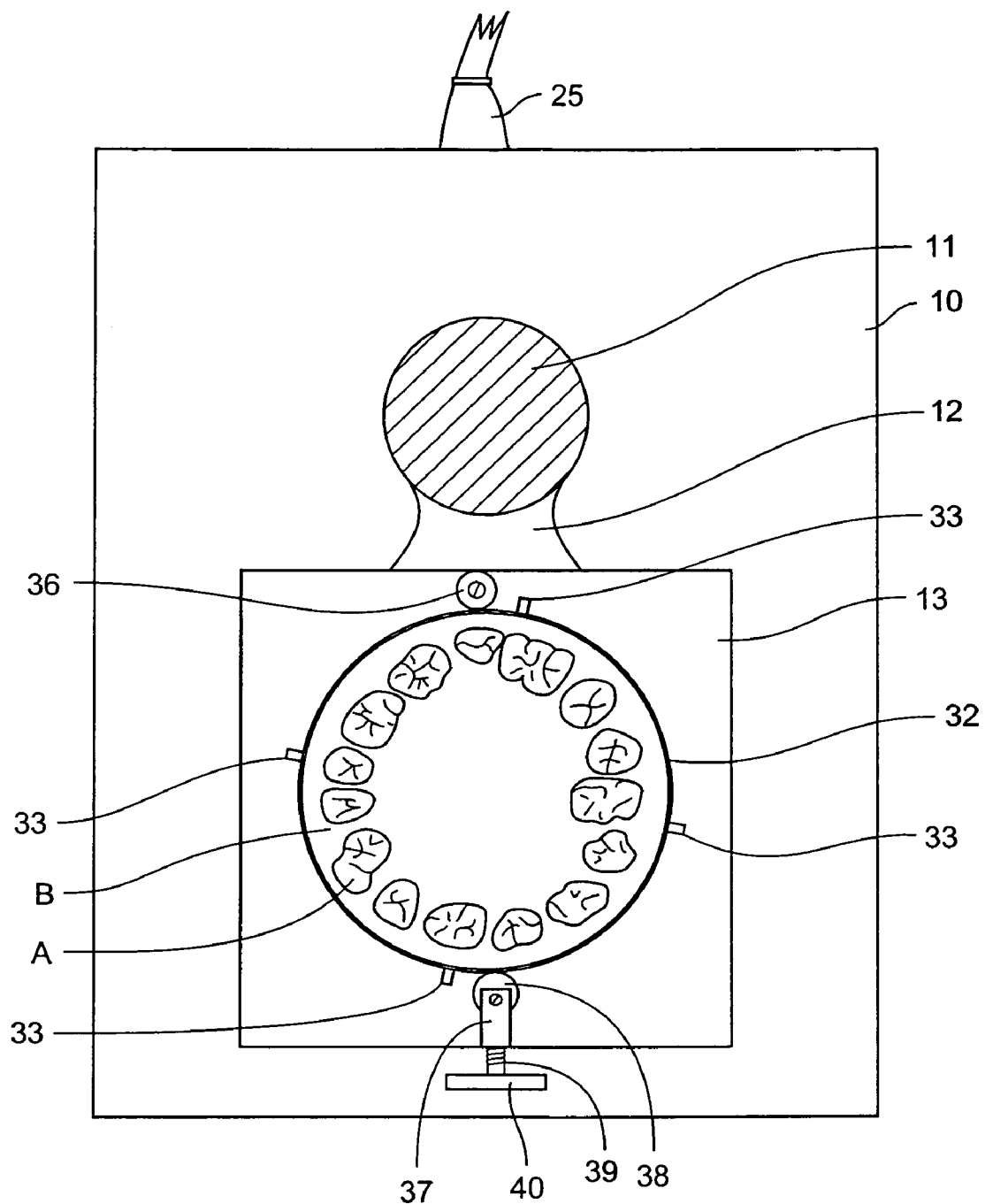
FIG. 5 shows an open surface of the tray as seen from above with a columnar post cut off between a fixed shaft that fixedly mounts an arm so as to allow the arm to rotate and the uppermost part of a multi-stage stopper in the dental crown polishing apparatus shown in FIG. 1.

FIG. 5 shows the open surface of the tray 32 as seen from above with the support post 11 cut off between the fixed shaft 15 that fixedly mounts the arm 14 so as to allow the arm 14 to rotate and the uppermost part of the multi-stage stopper 26.

The dental crowns A are arranged in a ring, that is, are arranged to match the arrangement of the brushes 22 mounted on the bottom of the brush assembly 21. However, it should be noted that, where the brushes 22 are arranged in a shape different from the shape of a ring, the crowns A may be arranged in a different yet matching layout as well.

Figure 6:
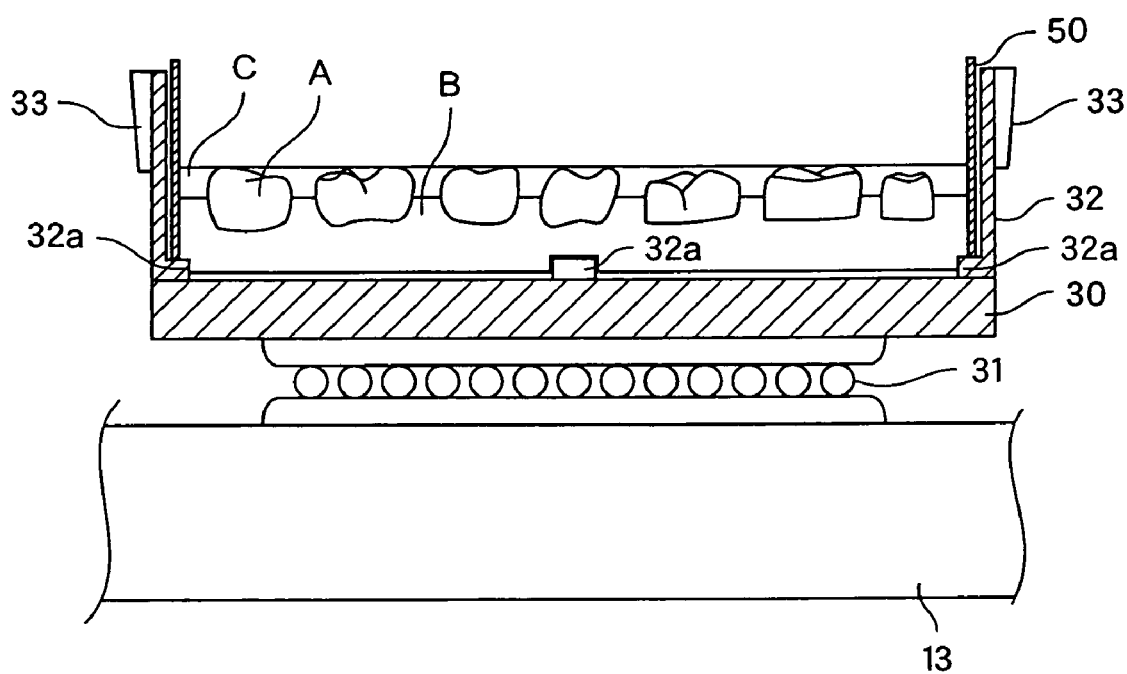
FIG. 6 shows an enlarged view of a partial cross-section of the tray periphery in the dental crown polishing apparatus shown in FIG. 1.

FIG. 6 shows an enlarged view of a partial cross-section of the periphery of the tray 32.

A plurality of stoppers 32a is provided around the periphery of the bottom of the tray 32 along the circumference of the bottom. A polishing target holding tray 50 for holding objects to be polished that is separate from the tray 32 is placed inside the tray 32. The bottom edge of the polishing target holding tray 50 is fixedly mounted on the interior of the tray 32 by the stoppers 32a. The stoppers 32a are so disposed as to project slightly inward from the outer diameter of the bottom of the polishing target holding tray 50. Accordingly, by pressing the polishing target holding tray 50 into the interior of the tray 32, it spreads the circle formed by the insides of the stoppers 32a so as to fixedly mount the polishing target holding tray 50 in the tray 32.

When polishing, the crowns A are placed in a circle in the polishing target holding tray 50 and held in place with the resin agent B. After the resin agent B hardens a polishing slurry C including a polishing agent is poured into the polishing target holding tray 50 to approximately the same height as the highest part of any of the crowns A.

Figure 7:
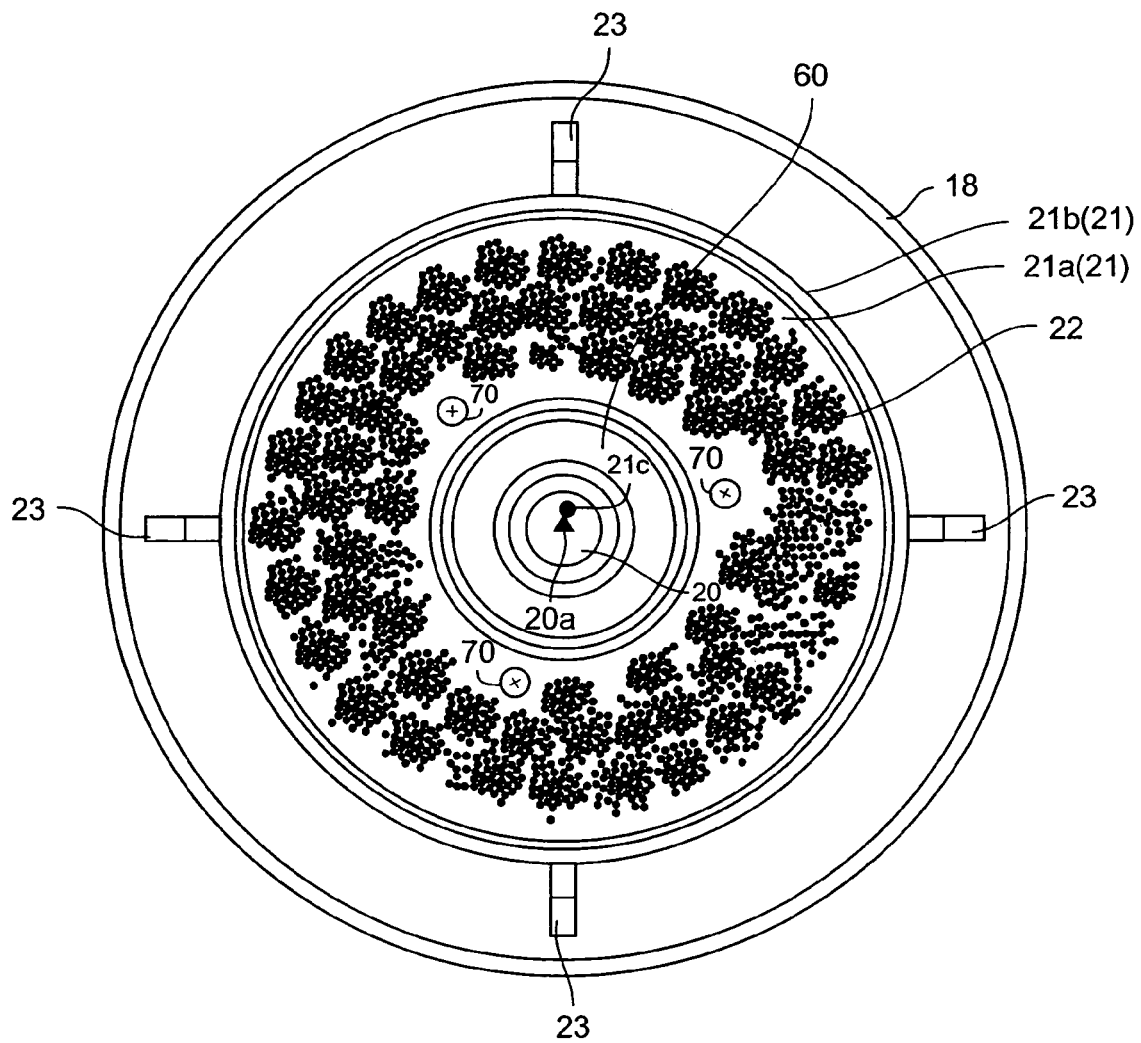
FIG. 7 shows a head in the dental crown polishing apparatus shown in FIG. 1 as seen from the brush side (that is, from below)

FIG. 7 shows the head 18 as seen from the brushes 22 (that is, from below).

The brush assembly 21 is composed of a first brush unit 21a and a second brush unit 21b located behind the first brush unit 21a, that is, behind the surface of the sheet of paper in which FIG. 7 is drawn. The brushes 22 are disposed in the shape of a ring in the first brush unit 21a. The first brush unit 21a is affixed to the second brush unit 21b by three screws 70 from the side of the brushes 22. The screws 70 are mounted in an area inside the ring of brushes 22. When the brushes 22 are worn out, the screws 70 are removed and the first brush unit 21b can be detached from the second brush unit 21b. A new first brush unit 21a is then mounted on the second brush unit 21b.

Next, the state of connection between the rotary shaft 20 coupled to the motor 19 and the brush assembly 21 is described.

The rotary shaft 20 is mounted on the brush assembly 21 through a disc-shaped ball bearing assembly 60. The axis of the rotary shaft 20 is the central point 20a (indicated by a black triangle) shown in FIG. 7. The center of the ball bearing assembly 60, which is also the center of the brush assembly 21, is the central point 21c (indicated by a black dot) shown in FIG. 7. Thus, the rotary shaft 20 and the ball bearing assembly 60 are not mounted concentrically. As the rotary shaft 20 rotates, the inner cylinder of the ball bearing assembly 60 rotates in orbital fashion. As a result, the brush assembly 21 also moves in orbital fashion in FIG. 7. However, it should be noted that the outer periphery of the ball bearing assembly 60 and the brush assembly 21 do not rotate at same rate as the inner periphery of the ball bearing assembly 60. Next, this point is described in detail.

Figure 8:
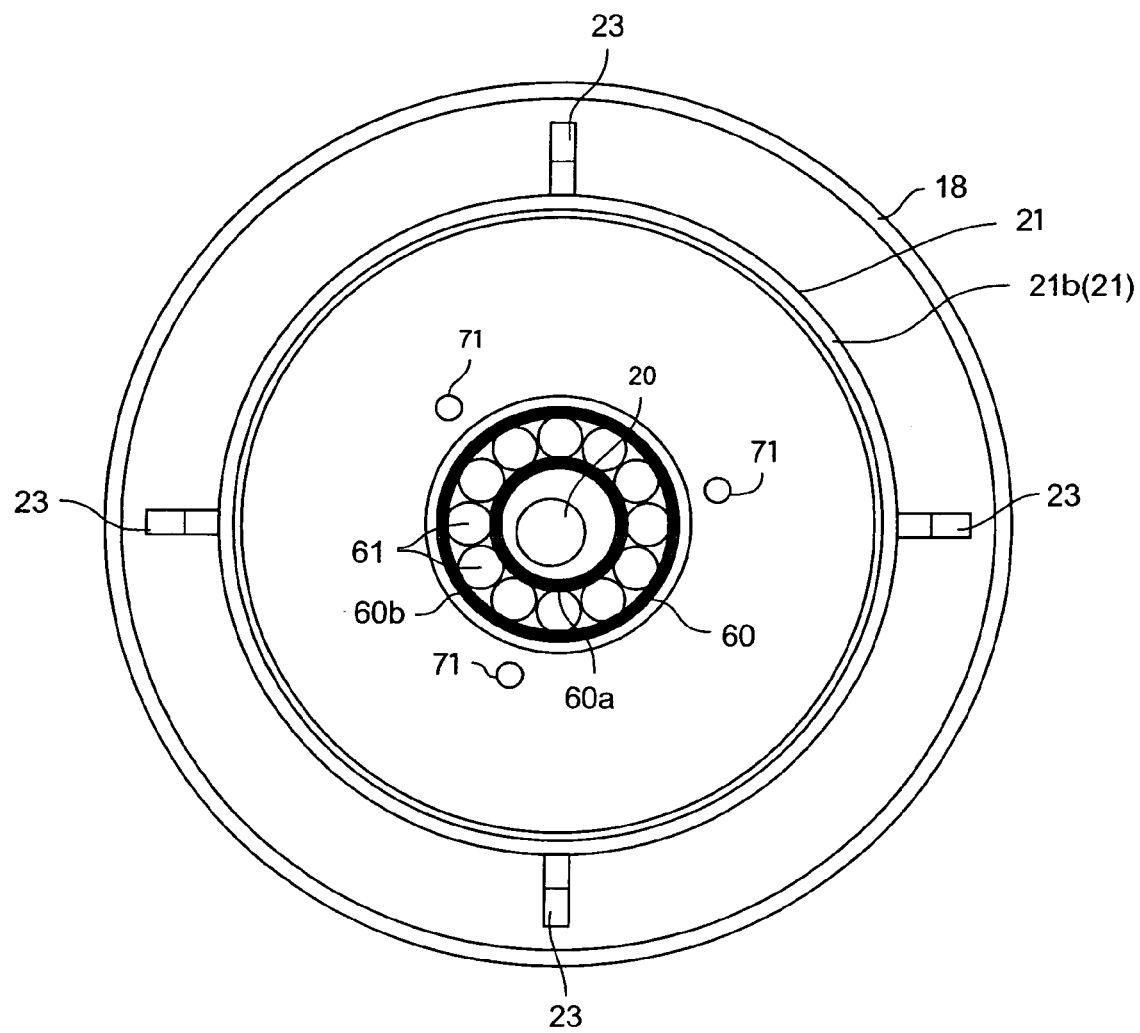
FIG. 8 shows the first brush unit removed so as to allow the interior of the ball bearing assembly to be seen in the state shown in FIG. 7.

FIG. 8 shows the first brush unit 21a removed so as to allow the interior of the ball bearing assembly 60 to be seen in the state shown in FIG. 7.

The ball bearing assembly 60 has a double cylinder construction comprised of an inner cylinder 60a (the part shown by the thick black line outside the rotary shaft 20) and an outer cylinder 60b (the part shown by the second thick black line counting in from the screw 71). A number of balls 61 are crammed into an annular space between the inner cylinder 60a and the outer cylinder 60b so as to contact each other. Grooves, not shown, are formed on the outer surface of the inner cylinder 60a and the inner surface of the outer cylinder 60b, and the rotary shaft 20 and the balls 61, and the balls 61 and the brush assembly 21, respectively, contact each other through these grooves.

As the rotary shaft 20 rotates, the balls 61 contacting the rotary shaft 20 move in the annular space and revolve while rotating. As the ball bearing assembly 60 moves in orbital fashion due to the rotation of the rotary shaft 20, the brush assembly 21 also similarly moves in orbital fashion. However, because the brush assembly 21 contacts the ball bearing assembly 60 through the balls 61, substantially none of the rotational force of the motor 19 is transmitted to the brush assembly 21. In other words, the inner cylinder of the ball bearing assembly 60 spins freely with respect to the brush assembly 21. However, since the ball bearing assembly 60 moves in orbital fashion, the brush assembly 21 moves in orbital fashion.

In reality, there is friction resistance at the portion of contact between the balls 61 and the brush assembly 21. Therefore, the brush assembly 21 also receives a force exerted in the circumferential direction by the rotation of the rotary shaft 20. Consequently, the brush assembly 21 moves in a way that combines both orbital movement and rotation. It should be noted that the frictional force between the balls 61 and the brush assembly 21 is very small, and thus the brush assembly 21, very unlike the high rpm of the motor 19, rotates slowly, at the rate of approximately 5-10 rotations per minute. The foregoing brush assembly 21 rpm is one example thereof, and can increase or decrease depending on the size of the frictional force with the balls 61.

Next, the orbital movement of the brush assembly 21 is described by using some drawings.

Figure 9:
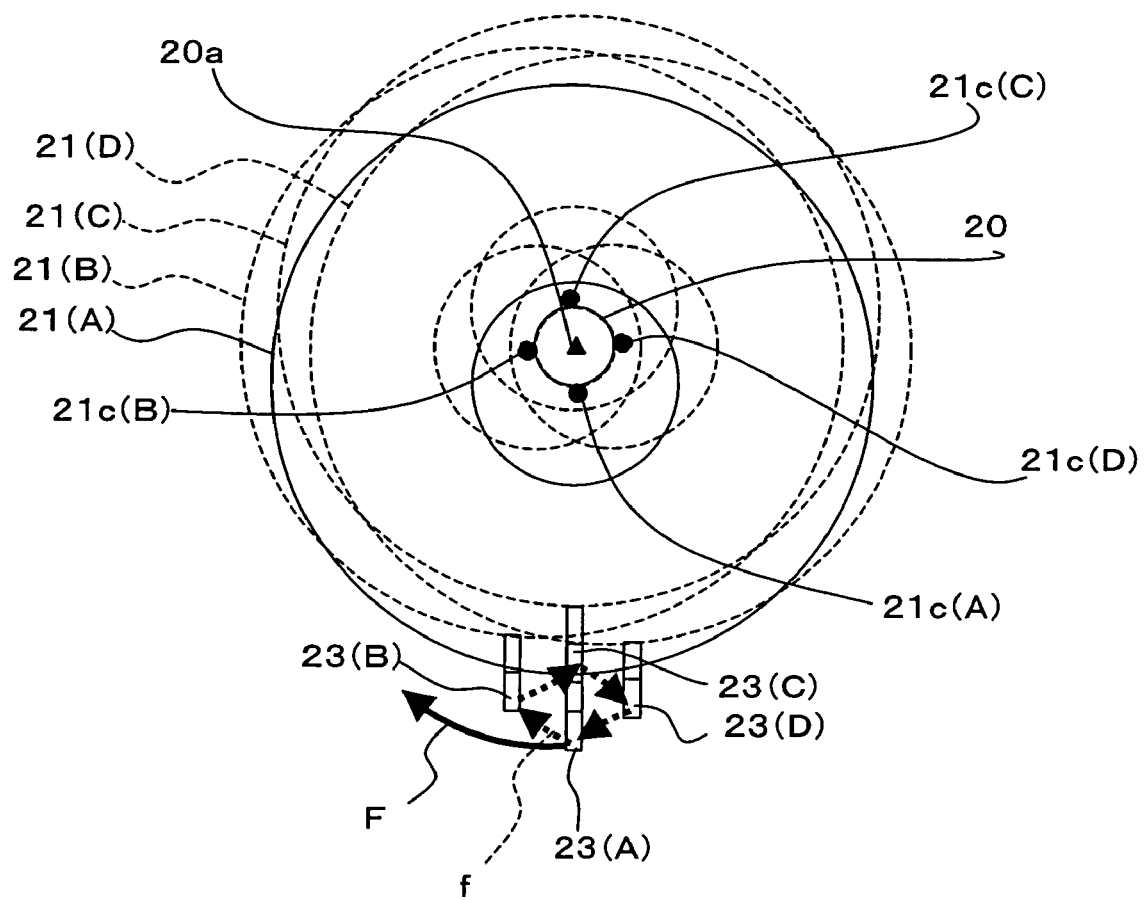
FIG. 9 is a diagram illustrating the ideal movement and the actual movement of the brush assembly in the state shown in FIG. 7.

FIG. 9 is a diagram illustrating the ideal movement and the actual movement of the brush assembly 21. It should be noted that, in FIG. 9, the movement of the brush assembly 21 is simplified as much as possible in order to facilitate an understanding of that movement, and thus only one of the four first projecting members 23 is considered and its movement traced.

In an ideal state in which the friction between the balls 61 inside the ball bearing assembly 60 and the brush assembly 21 is zero, in the case that the rotary shaft 20 (whose axis is the central point 20a) rotates clockwise once, when such a rotation is divided into four steps of 90 degrees each, the brush assembly 21(A) moves from an initial state indicated by the solid line and moves in orbital fashion to the positions indicated as brush assembly 21(B), brush assembly 21(C) and brush assembly 21(D). At this time, the center of the brush assembly 21 (whose center is the central point 21c) moves to the positions indicated by central point 21c(A), central point 21c(B), central point 21c(C) and central point 21c(D). Furthermore, as shown by the dotted line arrow f, the first projecting member 23 similarly moves to the positions indicated by first projecting member 23(A), first projecting member 23(B), first projecting member 23(C) and first projecting member 23(D).

However, in reality, unlike the ideal state described above, the friction between the balls 61 inside the ball bearing assembly 60 and the brush assembly 21 is not zero, and consequently, the brush assembly 21 also rotates as it receives the torque of the balls 61 that are themselves revolving due to the rotation of the rotary shaft 20. Therefore, the first projecting member 23 moves in the direction of "F" indicated by the solid line arrow while moving along the direction of the dotted line arrow f, in FIG. 9.

By the orbital movement of the brush assembly 21 described above, as the four first projecting members 23 move in a way that combines the movements indicated by the dotted line arrow f and the solid line arrow F, the second projecting members 33 that contact the first projecting members 23 receive forces exerted in the direction of the solid line arrow F and the dotted line arrow f by the first projecting members 23. Although the tray 32 is rotatably mounted via the ball bearing assembly 31, it is structurally incapable of moving laterally. Accordingly, the second projecting members 33 receive only a force exerted in the circumferential direction indicated by the solid line arrow F by first projecting members 23. As a result, the tray 32 rotates.

In addition, since the first projecting members 23 and the second projecting members 33 contacting each other but are not fixedly attached to each other, the tray 32 and the brush assembly 21 rotate to the same direction, but not in the same speed. When the first projecting members 23 and the second projecting members 33 are not in contact with each other, the tray 32 does not receive the force for the circumferential direction from the brush assembly 21. Then, the first projecting members 23 and the second projecting members 33 are in contact with each other again, and the tray 32 receives the force for the circumferential direction. The tray 32 rotates at approximately the same rpm with the brush assembly 21, that is, at approximately 5-10 revolutions per minute.

As described above, by setting multiple crowns A in the tray 32, by supplying a polishing agent to the tray 32 and by moving the brushes 22 orbitally, multiple crowns A are polished at same time. Since the brushes 22 rotate at a different speed from the tray 32 with orbital movement, the crowns A are polished with contacting the several positions of the brushes 22. Therefore, multiple crowns A of different unevenness can all be polished cleanly.

In addition, the first projecting members 23 which project from the brush assembly 21 are provided as the power transmission means for transmitting the drive of the motor 19 from the brush assembly 21 to the tray 32, and furthermore, the second projecting members 33 which project from the periphery of the tray 32 are provided as a passive means for accepting the torque from the brush assembly 21. Therefore, as the brush assembly 21 equipped with the brushes 22 moves orbitally, the driving force of the brush assembly 21 exerted in the circumferential direction of the tray 32 is transmitted easily to the tray 32 using a simple structure, and thus there is no need to provide a drive source for rotating the tray 32.

In addition, the ball bearing assembly 31 disposed between the tray 32 and the pedestal 13 beneath the tray 32 is provided as the rotation permitting means for permitting the tray 32 to rotate, and thus the tray 32 rotates smoothly by receiving the circumferential direction drive force exerted by the brush assembly 21.

In addition, the shaft 39 and the knob 40 are provided as the rotation adjustment means when in contact with the tray 32 for adjusting the rotation of the tray 32, and thus when the tray 32 rotates by receiving the drive force from the brush assembly 21, the resistance to the rotation can be adjusted. Therefore, it is possible to adjust the rpm of the tray 32 depending on the polishing conditions.

In addition, the knob 27 and the multi-stage stopper 26 are provided as a means for the tray height adjustment means for adjusting the distance of the tray 32 from the brush assembly 21. Thus, it is possible to adjust the distance between the brushes 22 and the crowns A accurately even when the crowns A are not set in the tray 32 at designated height. By adjusting the height of the tray 32 according to the extent of polishing, a variety of polishing conditions can be achieved.

In addition, the handle 17, the shaft 16, the fixed shaft 15 and the arm 14 are provided as means for adjusting the angle of the brushes 22 with respect to the opening surface of the tray 32. Thus, by setting the brushes 22 at a slight angle, it is possible to thoroughly polish even the deepest grooves of the crowns A, even if there is wide variation in the depth of the grooves in the uneven parts of the crowns A.

It should be noted that although one embodiment of the dental crown polishing apparatus according to the present invention is described above, the present invention is not limited to the above-described embodiment and can be implemented in a variety of variations and embodiments.

For example, instead of putting the polishing slurry (including polishing agent) into the tray 32, alternatively, the polishing slurry may be supplied continuously or intermittently to the brush assembly 21. Moreover, alternatively, the polishing agent may be fixed to the brushes 22 and only a fluid such as water or the like can be put in the tray 32 or water or other fluids can be supplied continuously or intermittently from the brush assembly 21.

In addition, the brushes 22 need not be arranged on the brush assembly 21 in the shape of rings, and alternatively, may be arranged in a circle or in a multi-angular shape. Moreover, the-brush assembly 21 need not be composed of the first brush unit 21a and the second brush unit 21b, and alternately may be a single unit. Moreover, the tray 32 need not be subjected to torque from the brush assembly 21, and alternatively may be made to rotate differently from the brush assembly 21 by the motor 19 or by a separate power source.

Alternatively, the power transmission means may be connected to the brush assembly 21 in the form of a projection contained within the tray 32. In that case, preferably, the passive means is located inside the tray 32 in the form of a projecting part capable of contacting the power transmission means.

In addition, the passive means need not be the same panel-like projecting members as the power transmission means. Thus, alternatively, a groove formed along the outer periphery of the tray 32 may be employed as the passive means. Where projecting members like the first projecting members 23 are employed, the tray 32 can be rotated by contacting the tips of the projecting members against the interior of the groove. Transmission of power is facilitated if the projecting members are composed of soft rubber. Furthermore, the bottoms of the brush assembly 21 and the tray 32 are not limited to circular shapes and thus alternatively may have other shapes.

The rotation permitting means need not be the ball bearing assembly 31, and alternatively may comprise a rotary shaft inserted into a hole formed in the center of the tray mounting plate 30. Moreover, where there is no tray mounting plate 30 and only the tray 32 is placed directly on the pedestal 13, a hole may be provided in the tray 32 and a rotary shaft inserted in the hole as the rotation permitting means.

The rotation adjustment means need not be the means for controlling the rotation of the tray 32 by a method of adjusting the force exerted on the roller 38, and alternatively (by a method that adjusts the force exerted on the tray mounting plate 30) may be a means for controlling the rotation of the tray 32. Moreover, an arrangement in which something is pressed against the tray 32 or a portion connected to the tray 32 at a location other than the tray mounting plate 30 as a brake to control the rotation of the tray 32.

Adjusting the height of the pedestal 13 need not be the only means for adjusting the height of the tray 32. Alternatively adjusting the height of just the tray 32 or just the tray mounting plate 30 may be the means for adjusting the height of the tray 32. Furthermore, where the tray height adjustment means can be implemented not by adjusting the force with which the ring member 12 is tightened against the support post 11 by rotation of the knob 27 so as to raise or lower the pedestal 13 or fix it at a desired position but by setting the frictional force or the engaging force between the ring member 12 and the support post 11 so that the ring member 12 does not descend naturally under its own weight and raising and lowering the ring member 12, the ring member 12 may be moved up and down with a force greater than the force with which the ring member 12 is kept from descending under its own weight. Moreover, the ring member 12 needs not be moved manually, and may alternatively be movable vertically by electric power.

The brush angle adjustment means need not be means for changing the angle between the brushes 22 and the crowns A by the inclination of the head 18, and alternatively may be a means for tilting only the brush assembly 21 or only the brushes 22. Moreover, even when changing the angle of the head 18, instead of rotating the arm 14 with respect to the support post 11, alternatively the brush angle adjustment means may be implemented by tilting the head 18 with respect to the arm 14. Moreover, instead of comprising the shaft 16, the handle 17 and the two planar projecting parts 14a, 14b, alternatively the brush angle adjustment means may be implemented by increasing the frictional force between the fixed shaft 15 and the hole in the arm 14 and either manually or electrically rotating the arm 14 around the fixed shaft 15.

Figure 10:
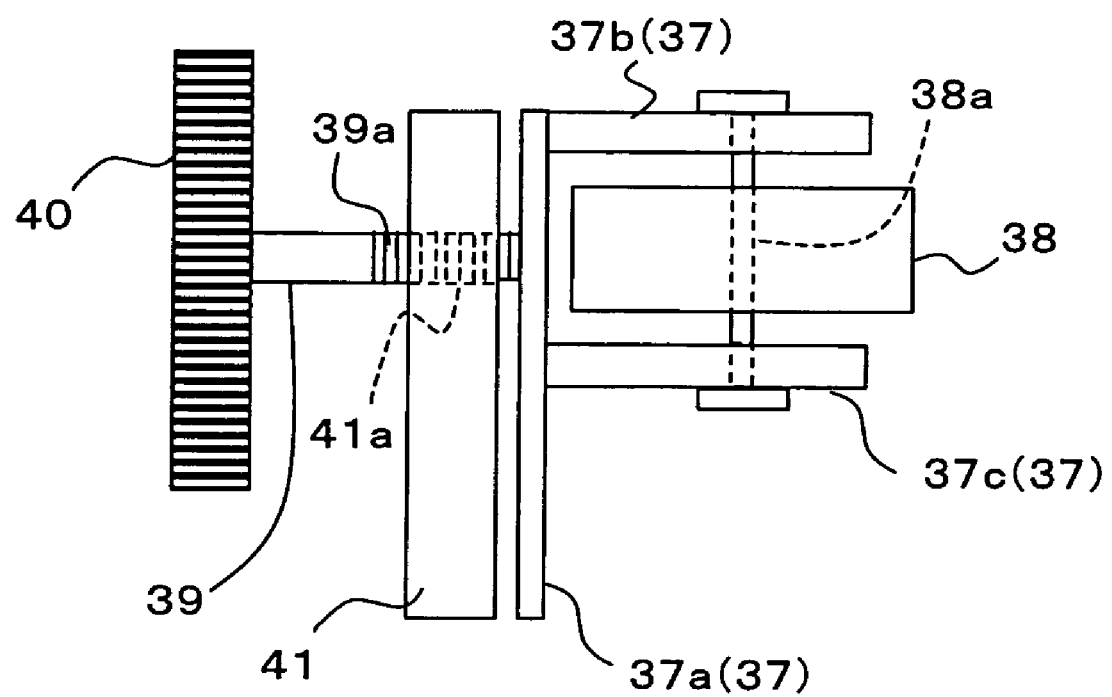
FIG. 10 shows an enlarged view of the area of the roller mounting plate different from that shown in FIG. 3.
Figure 11:
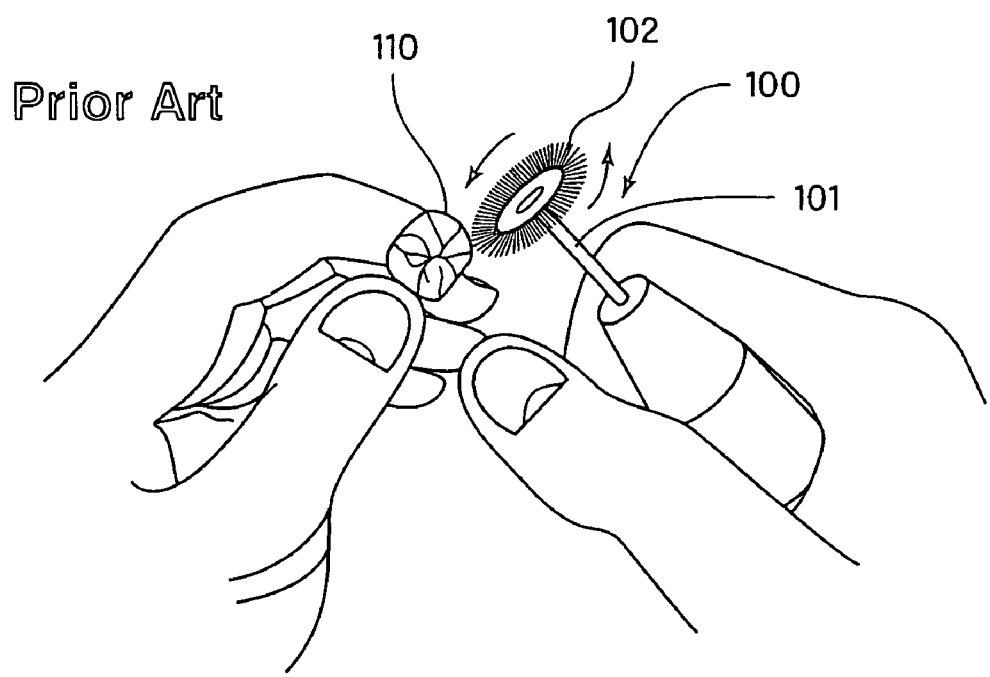
Figure 12:
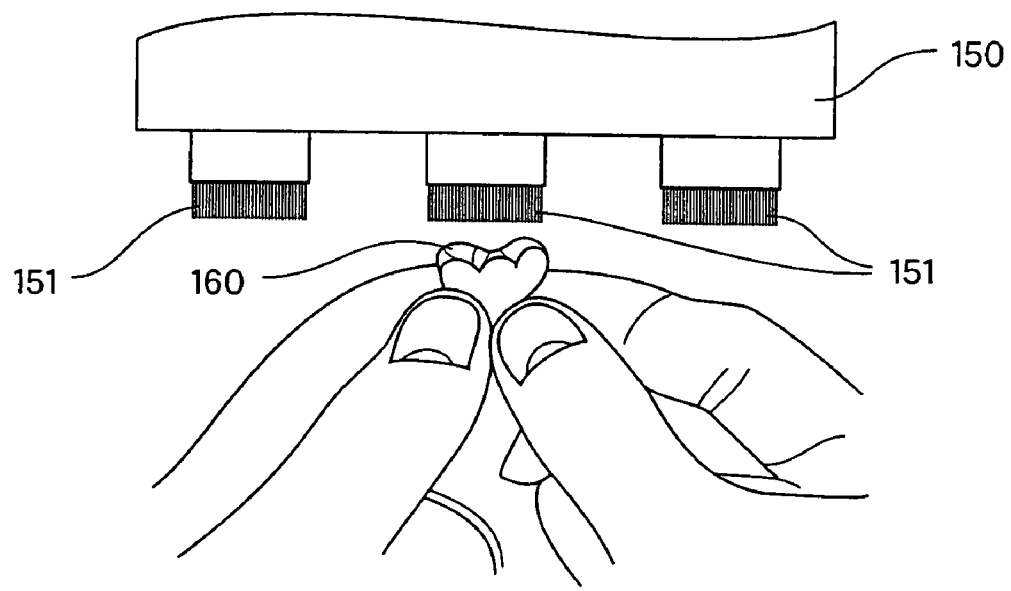
FIG. 12 is a diagram illustrating a method of polishing a crown or the like using the polishing apparatus previously invented by the inventor of the present invention.

In addition, the roller 38 shown in FIG. 3 may be provided in the structure shown in FIG. 10 so as to restrict the rotation of the tray mounting plate 30. FIG. 10 shows an enlarged view of the area of the roller mounting plate in a state different from that shown in FIG. 3. The roller mounting plate 37 shown in FIG. 10 comprises the fixed vertical panel 37a which extends perpendicularly upward from the pedestal 13 and two horizontal panels 37b and 37c extending substantially parallel to the top of the pedestal in the direction of the tray mounting plate 30 from the vertical panel 37a. The two horizontal panels 37b, 37c are fixedly mounted on the vertical panel 37a separated by a predetermined interval in the vertical direction. The roller 38, which is penetrated through its central axis by the rotary shaft 38a mounted perpendicular to the two horizontal panels 37b, 37c, is provided between the two horizontal panels 37b and 37c. The roller 38 is mounted between the horizontal panels 37b and 37c so as to be rotatable while contacting the periphery of the tray mounting plate 30.

The tip of the shaft 39 contacts the vertical panel 37a. The knob 40 is mounted on the end of the shaft 39 opposite the tip that contacts the vertical panel 37a. Screw threads 39a are cut into the shaft 39 over a predetermined length from the tip of the shaft 39, and this threaded portion 39a is screwed into a threaded through-hole 41a provided on a plate 41 disposed on the outer side of the roller mounting plate 37. Accordingly, as the knob 40 is turned and the shaft 39 is screwed toward the back of the apparatus, the tip of the shaft 39 pushes the vertical panel 37a so as to strongly contact the roller 38 against the tray mounting plate 30, which causes the resistance to the rotation of the tray mounting plate 30 to increase.

As many apparently widely different embodiments of the present invention can be made without departing from the spirit and scope thereof, it is to be understood that the invention is not limited to the specific preferred embodiments described above thereof except as defined in the claims.

What is claimed is:

1. A dental crown polishing apparatus comprising:
a motor;
a ball bearing assembly arranged around a motor shaft of the motor and equipped with a plurality of balls which rotate on its axis and circularly move around the motor shaft by receiving torque from the motor shaft;
a brush assembly mounted on the outer periphery of the ball bearing assembly, equipped with brushes, that connect the plurality of balls to rotate and that have bristles in the same direction as an axial "direction of the rotation of the brush assembly"; and
a tray mounted opposite and open to the brush assembly so as to direct a crown toward the brushes,
wherein the motor shaft is fixedly mounted at a position offset from the center of the brush assembly,
the brush assembly is able to move in orbital fashion by the rotation of the motor,
the tray is able to rotate separately from the brush assembly, the rotation of the tray is not synchronous with the rotation of the brush assembly, and,
dental crown polish is achieved by an orbital movement of the brushes;
wherein:
the brush assembly comprises power transmission means for transmitting torque to the tray;
the tray comprises passive means for receiving torque from the power transmission means and rotation permitting means for permitting the tray to rotate, and
the tray intermittently receives force in the direction of rotation by receiving an eccentric drive from the brush assembly through the passive means and rotates separately from the brush assembly.

2. The dental crown polishing apparatus according to claim 1 wherein the power transmission means comprises a first projecting member projecting from the periphery of the brush assembly and the passive means comprises a second projecting member projecting from the periphery of the tray.

3. The dental crown polishing apparatus according to claim 1 wherein the rotation permitting means is a ball bearing assembly disposed between the tray and a pedestal positioned beneath the tray.

4. The dental crown polishing apparatus according to claim 1, further comprising rotation adjustment means for adjusting the rotation of the tray.

5. The dental crown polishing apparatus according to claim 1, further comprising tray height adjustment means for adjusting the distance of the tray from the brush assembly.

6. The dental crown polishing apparatus according to claim 1, further comprising brush angle adjustment means for adjusting a horizontal angle of the brush with respect to an open surface of the tray.

7. The dental crown polishing apparatus according to claim 2, wherein the rotation permitting means is a ball bearing assembly disposed between the tray and a pedestal positioned beneath the tray.

8. The dental crown polishing apparatus according to claim 2, further comprising rotation adjustment means for adjusting the rotation of the tray.

9. The dental crown polishing apparatus according to claim 2, further comprising tray height adjustment means for adjusting the distance of the tray from the brush assembly.

10. The dental crown polishing apparatus according to claim 2, further comprising brush angle adjustment means for adjusting a horizontal angle of the brush with respect to an open surface of the tray.

* * * * *